United States Patent [19]

Lehneis et al.

[11] Patent Number: 4,520,512
[45] Date of Patent: Jun. 4, 1985

[54] ARTIFICIAL LIMB WITH AUTOMATIC RELEASE FOR FREE ROTATION

[75] Inventors: Hans R. Lehneis, Roslyn; Robert G. Wilson, New York, both of N.Y.

[73] Assignee: New York University, New York, N.Y.

[21] Appl. No.: 300,256

[22] Filed: Sep. 8, 1981

[51] Int. Cl.³ .............................................. A61F 1/04
[52] U.S. Cl. ................................................. 3/22; 3/2; 3/12
[58] Field of Search .......................... 3/2, 4, 14, 22, 23, 3/24, 25, 26, 27, 28, 12, 12.1, 122, 12.3

[56] References Cited

U.S. PATENT DOCUMENTS

| | | | |
|---|---|---|---|
| 2,573,347 | 10/1951 | Mazzola | 3/24 |
| 2,661,479 | 12/1953 | Alderson | 3/12 |
| 3,351,955 | 11/1967 | Middleton | 3/22 |
| 3,833,942 | 9/1974 | Collins | 3/29 |
| 4,232,405 | 11/1980 | Janovsky | 3/12.3 |

Primary Examiner—Richard J. Apley
Assistant Examiner—D. J. Isabella
Attorney, Agent, or Firm—Darby & Darby

[57] ABSTRACT

An artificial limb having two limb members connected by a joint is provided with rotator members, comprising one of the limb members, which are relatively rotatable about an axis extending along the limb. A locking mechanism is provided which is movable from a locking position to a released position. In the locking position, the locking mechanism provides a rigid connection between the two rotator members and thereby prevents rotation. When moved to its released position, the locking mechanism is disengaged from at least one of the rotator members, thereby permitting relative rotation between them. The locking member is disposed on one limb member in the vicinity of the joint and is connected via a coupling member to a fixed connection point on the other limb member. Normal movement of the limb about the joint thereby achieves movement of the locking mechanism between its locking and released positions, via the coupling member, and achieves automatic release and locking of the limb with respect to rotation as the limb is bent and straightened.

17 Claims, 9 Drawing Figures

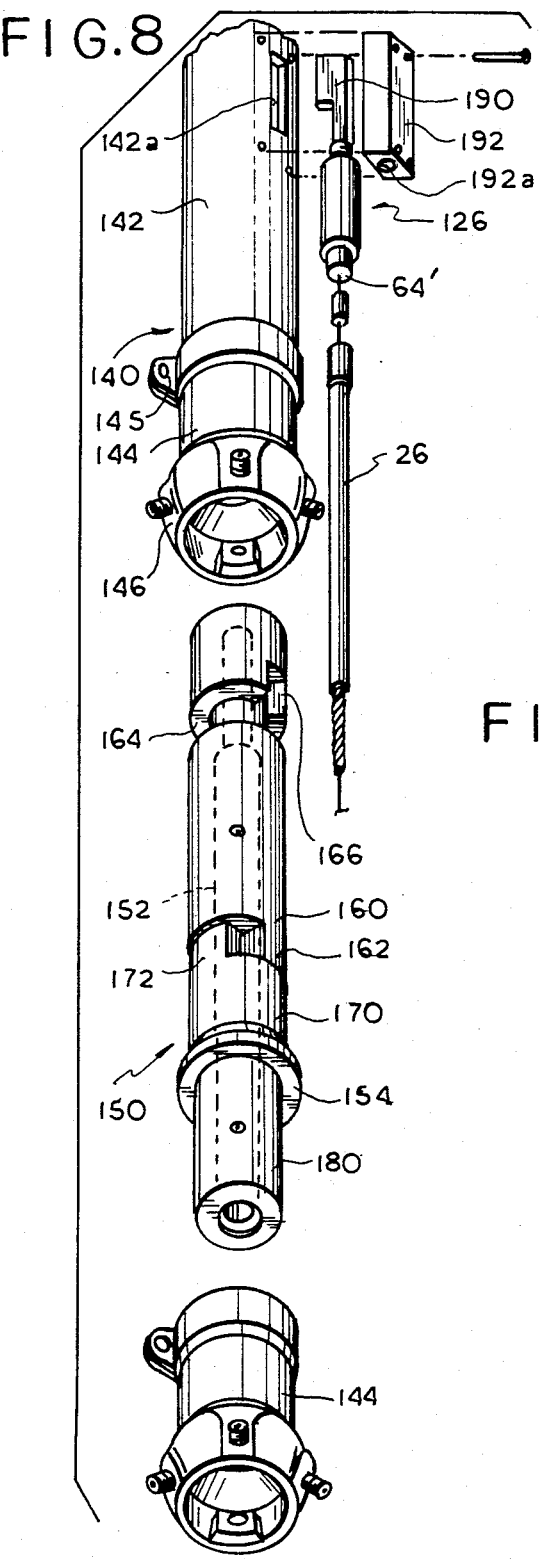
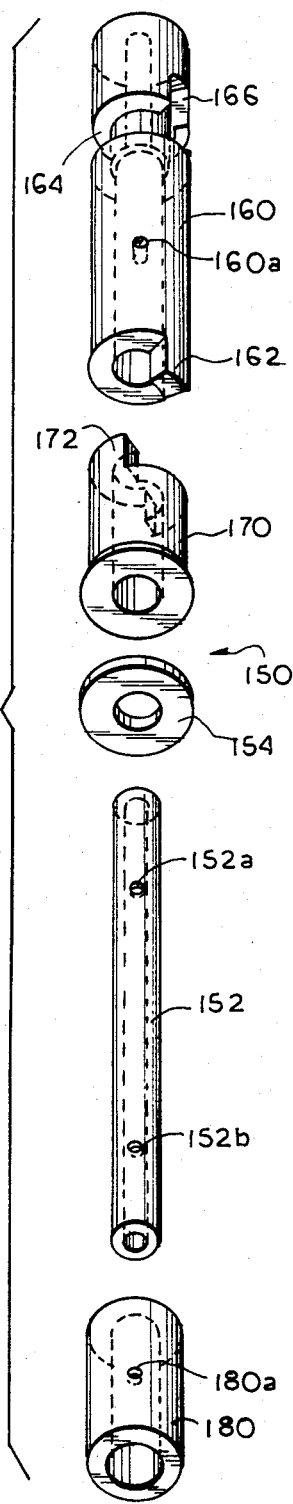
FIG.8
FIG.9

ARTIFICIAL LIMB WITH AUTOMATIC RELEASE FOR FREE ROTATION

The present invention relates generally to artificial limbs and, more particularly, concerns an artificial limb construction which is normally rigid, except for pivotal movement about the joints, and is actuated by the normal movement about one of the joints to enable and disable free rotation of the limb about an axis extending along its length.

Modern prostheses, such as artificial limbs, have enabled handicapped individuals to lead rather normal, productive lives. By providing an amputee with an artificial limb that simulates the operation of a real limb, it is possible, not only enabling him to perform his day-to-day tasks, but also to help him avoid the social embarrassments occasioned by his being recognized as an amputee.

Until now, those individuals with radical amputations have been unable to obtain entirely effective artificial limbs. For example, a patient whose leg has been amputated to a point above the knee joint would normally receive a prosthesis with an artificial knee joint and a lower leg, as well as a thigh portion having a "socket" in which the stump of his residual leg is securely received. Owing to the lack of a physical connection between the prosthesis and the patient's thigh bone, patient cannot transmit rotation of the hip joint to the prosthesis. As a result, the patient is unable to achieve any appreciable rotation of the artificial limb about an axis extending along the thigh. This makes it impossible for the patient to dress the prosthetic leg completely while wearing it. The patient is also unable to perform certain normal movements such as assuming a crossed-leg position while sitting, and experiences great difficulty getting in and out of an automobile.

In an attempt to overcome the difficulties which radical amputees experience with prosthetic legs, such devices have been provided with units permitting rotation of the leg about an axis extending along the thigh. Typically, such units, called femoral rotator units, are provided in the vicinity of the knee joint and directly above it. Inasmuch as the artificial leg must support the patient when he walks, it is extremely important that no rotary movement take place while he walks. The rotator unit is therefore provided with a locking mechanism which must be released by the patient when he wishes to rotate the leg about the thigh. This has been achieved by providing a release button at the side of the leg which the patient operates when he wishes to rotate the leg about the thigh. Although this releasable thigh rotator unit provides relief for the loss of normal hip rotation, it is hardly a satisfactory solution to the problem, since the patient must fumble with his leg to locate the release/lock button whenever he wishes to rotate it. This is not only inconvenient, but can prove socially embarrassing.

Similar rotator units have been provided for patients whose arms have been amputated to a point above the elbow joint in order to permit rotation about an axis extending along the upper arm (humeral rotation). In such humeral rotator units, locking and unlocking for rotation has been achieved by means of a cable which is connected from the rotator unit, across the patient's back, to the opposite shoulder. By moving the shoulder, the patient can then lock and unlock the humeral rotator for rotation. This type of device is also not entirely satisfactory, because it requires some conscious movement on the part of the wearer in order to lock and unlock the unit for rotation. This not only proves to be an inconvenience, but an embarrassment, since the patient can easily be identified as an amputee by the unusual shoulder movements required to achieve release and locking of the limb for rotation.

Broadly, it is an object of the present invention to provide an artificial limb having a rotator unit providing rotation about an axis extending along the limb, in which the unit may be enabled or disabled for rotation without the conscious intervention of the wearer to so operate the limb. It is specifically contemplated that the rotator unit should be enabled and disabled for rotation when certain predefined, normal movements of the limb itself are performed.

It is also an object of the present invention to provide an automatically operable rotator unit which can readily be incorporated into existing artificial limb constructions with a minimum of modifications.

It is a further object of the present invention to provide an artificial limb with an automatically lockable and releasable rotator unit which is convenient and reliable in use, yet relatively simple and inexpensive in construction.

In accordance with the present invention, an artificial limb having two limb members connected by a joint is provided with rotator members, comprising one of the limb members, which are relatively rotatable about an axis extending along the limb. A locking mechanism is provided which is movable from a locking position to a released position. In the locking position, the locking mechanism provides a rigid connection between the two rotator members and thereby prevents rotation. When moved to its released position, the locking mechanism is disengaged from at least one of the rotator members, thereby permitting relative rotation between them. The locking member is disposed on one limb member in the vicinity of the joint and is connected via a coupling member to a fixed connection point on the other limb member. Normal movement of the limb about the joint thereby achieves movement of the locking mechanism between its locking and released positions, via the coupling member and achieves automatic release and locking of the limb with respect to rotation as the limb is bent and straightened.

The foregoing brief description, as well as further objects, features and advantages of the present invention will be more completely understood from the following detailed description of presently preferred, but nonetheless illustrative, embodiments of the present invention, with reference being had to the accompanying drawing, wherein:

FIG. 8 is an exploded, perspective view of the component shown in FIG. 7; and

FIG. 9 is an exploded, perspective view of the rotor sub-assembly 150 of FIG. 8.

DETAILED DESCRIPTION

Figure 1:
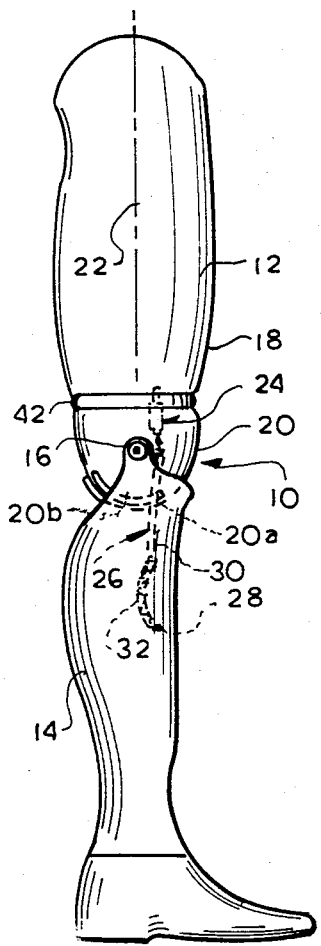
FIG. 1 is a side elevational view of an artificial leg embodying the present invention, the leg being shown in its upright or straightened position.

Two broad categories of artificial limbs or prostheses are generally known: the exoskeletal type and the endoskeletal type. An exoskeletal limb is formed with a hard outer shell which is shaped to simulate a real limb and is generally hollow. In an exoskeletal artificial leg, for example, the shell serves to support the wearer and to house the internal mechanisms of the leg. An endoskeletal prosthesis includes elongated, internal supporting members, similar to human bones, which are embedded in a foam material and covered by a resilient, flesh-like sheathe or stocking to simulate the appearance of a human limb. In an endoskeletal artificial leg, the structural members support the wearer, as well as all related mechanisms, and the foam and covering sheath conceal the structural members and mechanisms to lend a realistic appearance to the artificial limb. The present invention is applicable to both types of limbs, and exoskeletal and endoskeletal embodiments will be described separately.

FIGS. 1–5 illustrate an exoskeletal prosthesis in the form of an artificial leg 10 embodying the present invention. The prosthesis 10 is intended for use by a patient having a leg which has been amputated above the knee joint. As is typical, the prosthesis 10 includes: an upper leg portion or thigh 12 which is open on top to receive what remains of the patient's leg (the stump) from above; a lower leg portion 14 which incorporates an artificial foot; and a knee joint or pivot 16 connecting the portions 12 and 14 for relative pivotal movement.

The upper leg portion is divided into an upper segment 18 and a lower segment 20 which are connected so as to be relatively rotatable about an axis 22 extending along the length of the upper leg portion. Such rotation is commonly known as femoral (thigh) rotation. When the prosthesis 10 is in its straightened or upright position (shown in FIG. 1) the upper and lower thigh segments 18, 20 are fixedly retained against rotation by means of a locking mechanism 24, to be described in further detail below. The locking mechanism 24 receives a coupling member 26 which extends across the knee joint 16 to a connection point 28 on the lower leg 14, to which the coupling member 26 is affixed.

As can be seen in FIG. 1, coupling member 26 is preferably selected so as to be longer than the distance between the locking mechanism 24 and point 28 when the prosthesis 10 is upright. Preferably, coupling member 26 comprises a relatively unyielding component 30, such as a cable, and a resilient component 32, such as a tension spring. In FIG. 1, the length of the coupling member has been selected so that the spring 32 is under no tension.

The lower thigh segment 20 includes a surface 20a which extends substantially below the knee joint 16. When the prosthesis 10 is bent, as in FIG. 2, the surface 20a moves forward (to the right in FIG. 2) and, by virtue of a guide slot 20b within which the coupling member 26 is received, carries the coupling member with it. This has the effect of increasing the distance between locking member 24 and point 28 over the path followed by coupling member 26, thereby acting to place the spring 32 under tension, whereby the coupling member 26 applies a force to the locking device 24. As will be explained in detail below, this force acts to disable the locking device 24, thereby releasing the thigh segments 18, 20 for relative rotation about the axis 22. The lower leg 14 may then be pivoted with respect to the thigh 12, as shown in FIG. 3, to permit the wearer to accomplish such movements as crossing his legs or exiting from an automobile. Moreover, release of the leg for rotation is achieved without any conscious movement on the part of the wearer, but occurs automatically upon the leg being bent.

Figure 2:
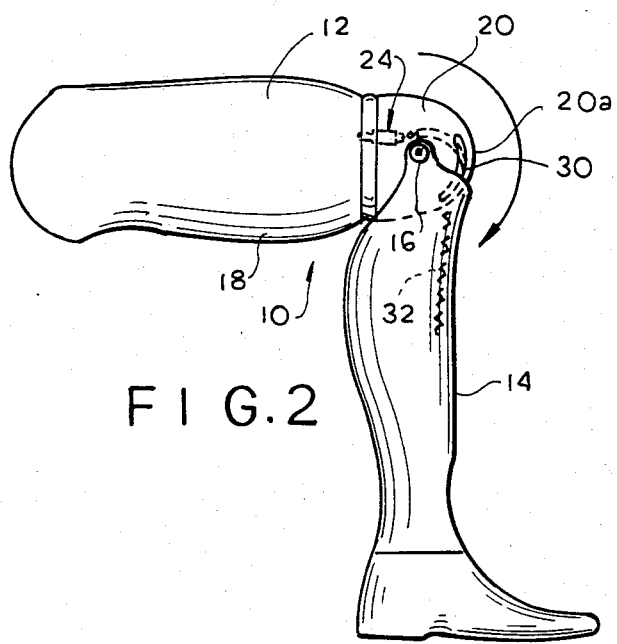
FIG. 2 is an elevational view, similar to FIG. 1, in which the leg is shown bent to an angle of approximately 90 degrees.
Figure 3:
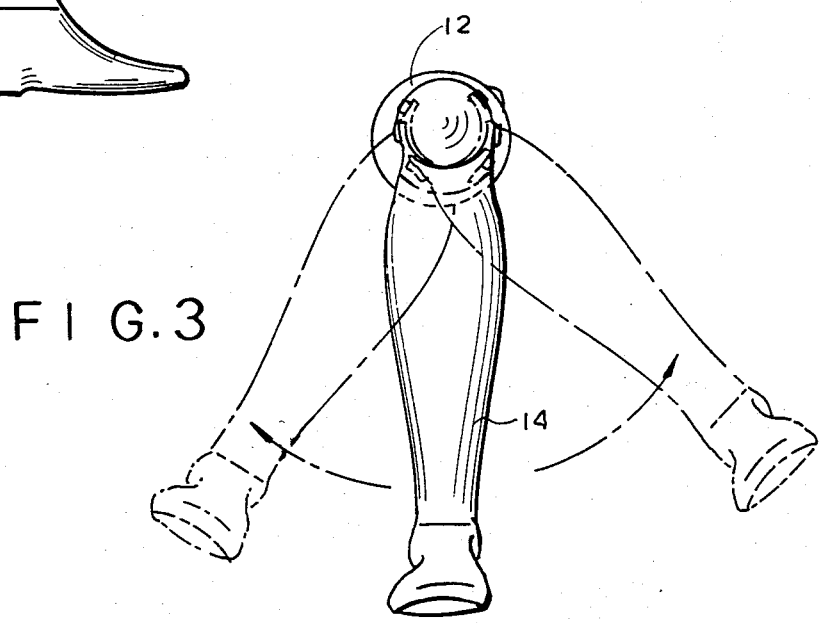
FIG. 3 is a front elevational view of the leg of FIG. 2 illustrating the manner in which the leg may be rotated about the thigh when it is brought to the bent position shown in FIG. 2.

In practice, the length of the coupling member 26 is preferably selected to achieve disablement of locking memeber 24 when the prosthesis 10 is placed in approximately a 90 degree position, as shown in FIG. 2. As a result, when the wearer stands up and straightens the leg somewhat from the 90 degree position, the force applied by coupling member 26 to locking mechanism 24 is reduced sufficiently to permit the locking device 24 to become activated once more. The thigh segments 18, 20 are once more secured against relative rotation after the lower leg is retrieved to a non-rotated position. Hence, the prosthesis 10 automatically locks itself against thigh rotation when the wearer straightens his leg.

Figure 4:
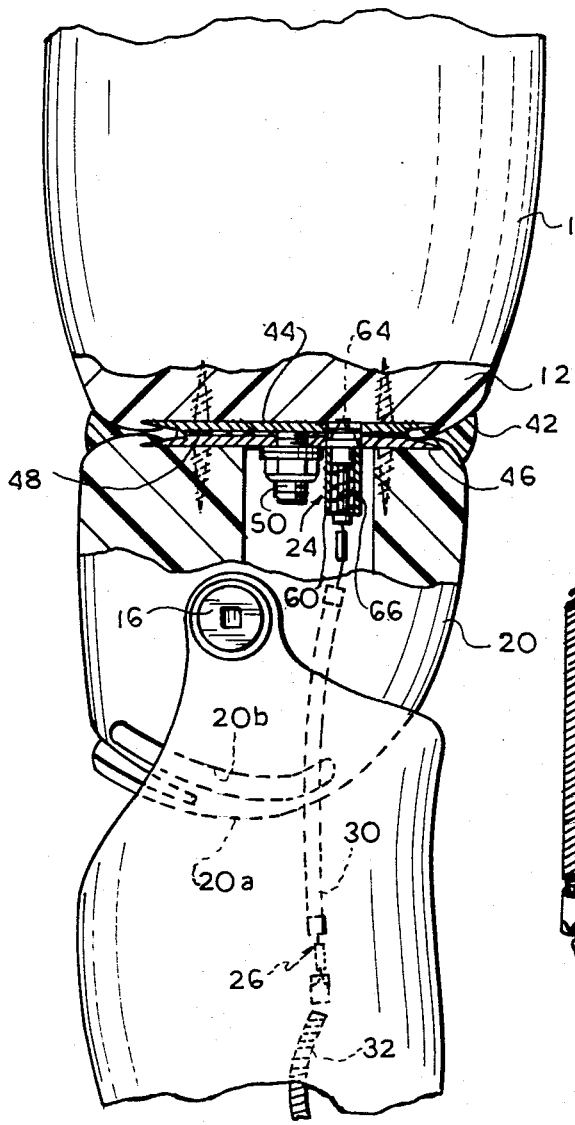
FIG. 4 is a side fragmentary view, on an enlarged scale, of the artificial leg as shown in FIG. 1, with parts being shown in section to illustrate constructional details.
Figure 5:
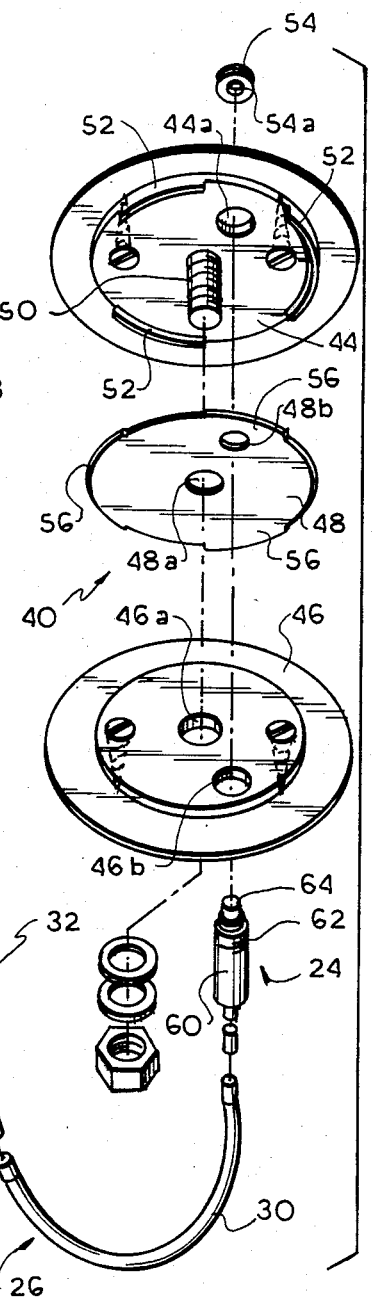
FIG. 5 is an exploded, perspective view illustrating the components of the automatically operable rotator unit incorporated in the artificial leg illustrated in FIGS. 1-4.

Referring now to FIGS. 4 and 5, there are illustrated the details of the mechanism for achieving thigh or femoral rotation and the cooperation of locking mechanism 24 therewith, as explained above. The femoral rotator mechanism, designated generally as 40, is concealed from view by a generally teroidal sealing member 42, which fills the gap between the upper and lower thigh portions 18, 20. The rotator mechanism broadly comprises: an upper plate member 44 secured at the bottom of upper thigh segment 18; a lower plate member 46 secured at the top of lower thigh segment 20 in opposed relationship to the upper plate member; and a disc-like bearing member 48 interposed between the upper and lower plate members 44, 46. The plate members 44, 46 can be made of any sturdy material, but are preferably made of aluminum or an aluminum alloy owing to the light weight of such metals. The plates 44, 46 may be secured to their respective thigh segments by any appropriate means, but are preferably laminated thereto. In the illustrative embodiment, additional fasteners in the form of screws have been provided to assure that the plates do not rotate with respect to their respective thigh segments.

Upper plate member 44 has a concentric stud 50 depending therefrom, which serves to hold the femoral rotator mechanism together and also defines the axis of femoral rotation. In addition, plate 44 has a plurality of circumferentially spaced depending walls 52 which served to retain the bearing member 48 against rotation with respect to the plate 44, as will be explained further below. Plate member 44 also includes a threaded hole 44a, which receives an externally threaded plug 54 having a tapered bore 54a.

Bearing member 48 is generally disc-shaped, but is provided with protruding, circumferentially spaced ears 56 dimensioned to be received with a close tolerance between the depending walls 52 of upper plate member 44. Bearing member 48 also has a concentric bore 48a dimensioned to receive stud 50 and a bore 48b positioned to align with hole 44a of upper plate member 44 when the ears 56 are received between the depending walls 52. Hence, when bearing member 48 is properly mounted with respect to upper plate 44, stud 50 protrudes through bore 48a, the ears 56 are received between the depending walls 52, so that member 48 must rotate with member 44, and the bore 48b is aligned with the bore 54a of plug 54.

Lower plate member 46 has a concentric bore 46a through which stud 50 passes and an internally threaded bore 46b, which receives locking member 24 for securement therein, as explained more fully below.

When the femoral rotator mechanism 40 is assembled, members 44 and 46 are in opposed relationship, with the member 48 interposed between them and the stud 50 extending through the bores 48a and 46a, to protrude below lower plate member 46. Assembly of the femoral rotating mechanism can then be completed by securing washers and a conventional locknut, or similar devices, to stud 50 (it should be noted, however, that sealing member 42 must be interposed between thigh segments 18 and 20 prior to assembling the femoral rotator assembly 40). The upper and lower thigh segments 18, 20 are then held together by means of stud 50 and its fasteners and are relatively rotatable, with stud 50 serving as an axle.

Locking member 24 broadly comprises: a cylindrical housing 60 having a threaded neck 62; a plunger 64 mounted for sliding movement within housing 60 and protruding through the bottom thereof to have coupling member 26 secured thereto; and a compression spring 66 interposed between the plunger 64 and the bottom of housing 60 so as to urge the plunger upward with respect to the housing. In addition, plunger 64 is retained within housing 60 by conventional means, not shown. In practice, locking member 24 is secured to bottom plate member 46 by threading neck 62 into aperture 46b. Housing 60 then projects downward from plate member 46 and the upper end of plunger 64 extends into bore 54a of plug 54.

It should be noted that the tip of plunger 64 is tapered. Preferably, this taper matches the taper of bore 54a. *It is then possible to secure plug 54 within upper plate member 44a* so as to achieve a close fit of plunger 64 within bore 54a. In this manner, the free play within femoral rotator 40 can be minimized, to assure that essentially no movement can take place between the segments 18 and 20 when the prosthesis 10 is upright, a time when the patient's weight is being supported and great stability is required.

From the foregoing description, it will be appreciated that, when the femoral rotator 40 is locked against rotation, coupling member 26 exerts no significant force on plunger 64, so that spring 66 urges the tip of the plunger into bore 54a. However, when prosthesis 10 is bent, as in FIG. 2, spring 32 causes coupling member 26 to exert a downward force on plunger 64. When this force exceeds the force of spring 66 (preferably when the prosthesis 10 is bent to an angle of approximately 90 degrees), plunger 64 will be pulled downward, out of aperture 54a, permitting relative rotation between plate members 44 and 46. Bearing member 56, which is preferably made of teflon, assures that frictional resistance to rotation is at a minimum and that the rotation is smooth.

When prosthesis 10 is returned to its upright position or is otherwise straightened, the force applied to plunger 64 by coupling member 26 is reduced, and spring 66 urges the plunger back towards upper plate member 44. If the prosthesis 10 is in a nonrotated position, plunger 64 will be aligned with aperture 54a, and locking member 24 will immediately lock the plate members 44 and 46 against rotation. Should the prosthesis 10 be in a rotated position, the top of plunger 64 will be urged against the bottom surface of bearing member 48. When the prosthesis 10 is then returned to its nonrotated position, plunger 64 will enter aperture 54a immediately, thereby locking up femoral rotator 40 against rotation.

From the foregoing description, it will be appreciated that the present invention provides a prosthetic limb which is automatically released and locked for rotation about an axis extending along its length by the normal bending movement of the limb. Moreover, no conscious action is required by the patient in order to achieve the release and locking, eliminating any inconvenience and embarrassment for the patient.

FIGS. 6–9 illustrate an endoskeletal prosthesis in the form an artificial leg 110 embodying the present invention. Like the prosthesis 10 of FIGS. 1–5, the prosthesis 110 is intended for use by a patient with a leg which has been amputated to a point above the knee.

The prosthesis 110 is constructed so as to be compatable with a modular system of endoskeletal prosthesis components which is available from Otto Bock Orthopedic Industry Inc. of Minneapolis, Minn. As is characteristic of endoskeletal devices, the prosthesis 110 has an internal framework 112 simulating the bones forming the skeletal structure of the human leg. This framework is embedded in a mass of foam material or padding 114 which fills in the shape of the leg and lends a human "softness" to it. The padding 114 is then surrounded by a sheath of flexible material 116 forming the "outer skin" of the leg.

The framework 112 broadly comprises: a thigh unit 118 incorporating femoral rotator mechanism described in detail below; a lower leg unit 120 including an artificial foot; and a knee joint unit 122 connecting the units 118 and 120 for relative pivotal movement. The prosthesis 110 also includes a locking mechanism 126 mounted on the thigh unit which normally locks the femoral rotator against movement, but is actuable through a coupling member 26, similar to coupling member 26 of prosthesis 10, to release the femoral rotator for rotation. The coupling member 26 is supported on guides 124,123 providing on thigh unit 118 and knee joint unit 122, respectively, and passes across the knee joint for connection to the lower leg unit by a conventional clamping means. As was the case with prosthesis 10, prosthesis 110 achieves automatic releasing and locking of the femoral rotator with bending and straightening of the leg 110 at the knee joint.

The lower leg unit 120 is entirely a standard Otto Bock assembly. It comprises an elongated tube 130 having a tube clamp 132 secured at either end. The lower tube clamp receives an ankle and foot unit for securement to tube 130, and the upper tube clamp is secured to the knee joint unit 122. The knee joint unit 122 is also a standard Otto Bock unit, but it is modified by the addition of the support and guide 123 for connecting member 26 which keeps the connecting member t a distance from the knee joint and also prevents it from moving laterally with respect to the leg. The thigh unit includes: a cup-shaped member 135 (a standard Otto Bock component), which is laminated into the lower end of the leg socket which receives the patient's stump; and a tubular rotator unit 139 having and Otto Bock tube clamp at either end. The lower tube clamp receives the knee unit and the upper tube clamp receives the cup-shaped member 135.

As best seen in FIG. 8, the femoral rotator unit 139 includes two major sub-assemblies: a housing sub-assembly 140 forming the stationary part of the rotator unit; and a rotor sub-assembly 150. The housing sub-assembly 140 is a standard Otto Bock sub-assembly comprising a tube 142 with a tube clamp 144 (identical to tube clamp 132) secured at either end. The upper tube clamp is shown only in FIG. 6. The tube 142 is modified by the provision of an axially oriented, elongated slot 142a in its side wall to permit the operation of locking mechanism 126, as will be explained in detail below. As will be appreciated from FIG. 8, the tube clamps of 144 are affixed on tube 142 by means of a conventional circumferential clamping means 145. Opposite the clamping means 145, each clamp includes a securing mechanism 146 incorporating four equally spaced setscrews. The upper securing mechanism couples the cup-shaped member 135 to tube 142, and the lower one receives the rotor sub-assembly 150 and secures it for rotation within housing sub-assembly 140.

Figures 6, 7:
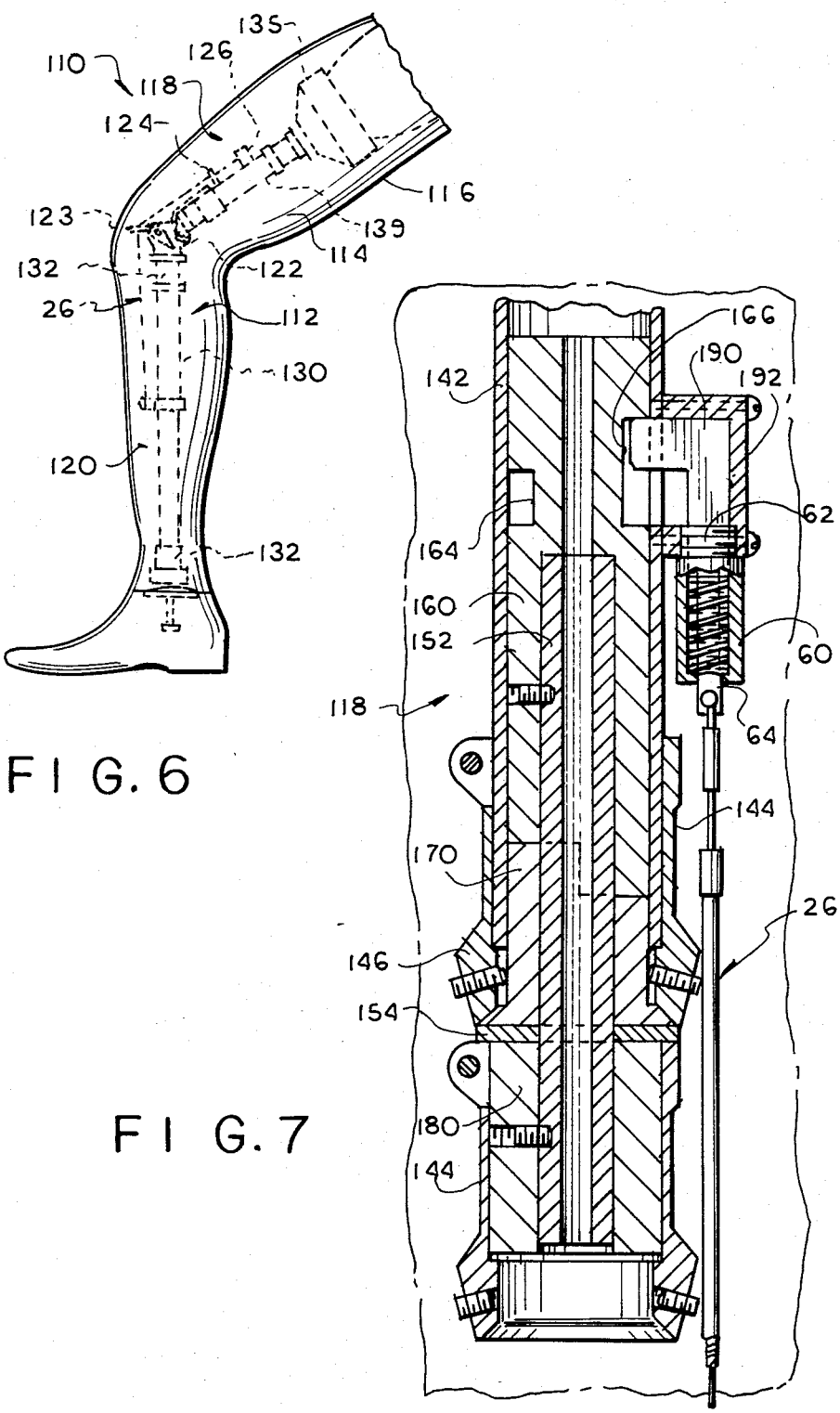
FIG. 6 is a side elevational view of a second embodiment of the invention, also in the form of an artificial leg.
FIG. 7 is a fragmentary sectional side view, on an enlarged scale, illustrating the components of the artificial leg of FIG. 6 which cooperate to achieve automatic rotation about the thigh.

As can be seen in FIGS. 7 and 9, the components of rotor assembly 150 are all coaxially mounted on a supporting shaft 152. These components include: a control sleeve 160, which assists in enabling and disabling femoral rotation; an upper bearing sleeve 170 and a lower bearing sleeve 180, which rotate relative to each other when femoral rotation takes place; and a bearing disc 154 interposed between the opposed end faces of bearing sleeves 170 and 180 to reduce friction and minimize wear. In addition, a conventional Otto Bock tube clamp 144 (not shown in FIG. 9) is mounted on lower bearing sleeve 180 to permit rotor unit 150 to be connected to knee unit 122. Bearing disc 154 is preferably made of Teflon TM, owing to the low coefficient of friction of that material, and the remaining components of the rotor unit 139 are preferably made of aluminum or an aluminum alloy, as are the Otto Bock components.

When rotor assembly 150 is assembled, control sleeve 160 is affixed to shaft 152 by means of a set screw (not shown) which is secured in the bores 160a and 152a provided in the control sleeve and shaft, respectively. Similarly, lower bearing sleeve 180 is secured to the opposite end of shaft 152 by means of a set screw (not shown) which is inserted into the apertures 180a and 152b provided in the sleeve and shaft, respectively. The upper bearing sleeve 170 is not secured to shaft 152, but is capable of rotating freely with respect to shaft 152. This rotation is, however, limited to an angle of less than 180 degrees as a result of interference between lateral faces of depending wall 162 of control sleeve 160 and upwardly projecting wall 172 of bearing sleeve 170. As can be seen in FIG. 8, when rotor assembly 150 is assembled, the lateral faces of these walls will engage during rotation to limit relative rotation between the sleeves 160 and 170.

After the rotor assembly 150 is completely assembled, it is inserted into housing assembly 140 so that sleeves 160 and 170 are completely enclosed therein, and the set screws of tube clamp 144 at the bottom of housing assembly 140 are tightened to secure bearing sleeve 170 within the housing assembly 140. It will be appreciated that, since bearing sleeve 170 is freely rotatable, over a limited angle of rotation, with respect to shaft 152, the components secured to shaft 152 will be rotatable with respect to housing assembly 140. In particular, the tube clamp 144 in which the ankle unit is secured is rotatable with respect to tube clamp 144 at the bottom of housing assembly 140, thereby achieving femoral rotation.

As best seen in FIG. 7, control sleeve 160 has a thicker wall than the other two control sleeves. The lower portion of control sleeve 160 is, however, provided with an enlarged inside diameter, so as to be capable of receiving the shaft 152. The upper portion of sleeve 160, in which the original wall thickness is maintained, is provided with a circumferential groove 164 and a radially extending slot 166 which intersects the groove. This slot 166 is aligned with the slot 142a of housing assembly 140 when the rotor assembly is secured in the housing assembly. Slot 166 is then able to receive a key member 190 which projects from locking assembly 126 through slot 142a and into slot 166. When the key 190 is so positioned, slot 166 may not be moved with respect to slot 142a, so that femoral rotation is not possible. However, through the action of coupling member 26 on locking member 126, key 190 may be moved axially out of slot 166 (downward in the drawing) and into groove 164. Key 190 is dimensioned so as to be received freely within groove 164, so that when key 190 moves into the groove, it becomes possible for slot 166 to move with respect to slot 142a, and femoral rotation is enabled. From the foregoing description, it will be appreciated that locking assembly 126 and control sleeve 160 cooperate to control enablement and disablement of femoral rotation.

Locking unit 126 is mounted on tube 142 of housing assembly 140 after the rotor assembly 150 is secured within the housing assembly 140. Control assembly 126 includes an enclosure 192 which is secured to tube 140 over slot 142a, for example by screws. In the bottom of enclosure 192, there is provided a threaded bore 192a which is dimensioned to receive the threaded neck 62 of a cylindrical housing 60 which is identical to housing 60 of FIG. 5. The locking member 126 further includes a spring 66 which is identical to spring 66 of locking member 24 of FIG. 5, and a plunger 64' which is similar to plunger 64 of locking member 24, except that the L-shaped key 190 is detachably mounted thereon (by conventional means, not shown), instead of a tapered tip. A connecting member 26 is received in the bottom of plunger 64', which is identical to connecting member 26 of FIG. 5.

From the discussion relating to FIG. 5, it will be appreciated that spring 66 acts to bias plunger 64' upwardly, thereby retaining key 190 within slot 166 of control sleeve 160. Bending of the knee joint causes connecting member 26 to assert a downward force on plunger 64', which, by design, overcomes the force of spring 66 when the knee joint is bent to approximately 90 degrees. This releases the prosthesis 110 for femoral rotation, as was the case with prosthesis 10. As with the prosthesis 10, straightening of the leg results in reduction of the downward force applied to plunger 64' by connecting member 26 and key 190 returns into slot 166 when the prosthesis 110 is returned to its non-rotated position.

Although preferred forms of the invention have been disclosed for illustrative purposes, those skilled in the art will appreciate that many modifications, substitutions, and additions may be made without departing from the scope and spirit of the invention as defined in the accompanying claims.

What is claimed is:

1. In an artificial limb of the type having a joint and incorporating a rotator unit for achieving rotation about an axis extending along the limb, said rotator unit being disposed in the vicinity of said joint and including a locking mechanism movable to enable and disable the rotation of said rotator unit, the improvement comprising a coupling mechanism connecting said locking mechanism to a fixed point on said limb, said rotating unit and fixed point being on opposite sides of said joint, said coupling mechanism extending along said limb and across said joint, and means for coupling the pivotal movement of said limb at said joint to said coupling mechanism to impart movement to said locking mechanism for enabling and disabling said rotation, whereby said enabling and disabling occur automatically when said limb is pivoted at said joint.

2. The improvement of claim 1 wherein said coupling mechanism includes a resilient member applying a force to said locking mechanism to achieve movement thereof for said enabling and disabling of said rotation, said force being produced by stressing said resilient member as a result of the movement of said limb about said joint.

3. The improvement of claim 2 wherein said coupling mechanism includes a tension spring forming at least a portion of an elongated coupling member extending across said joint, said coupling member being positioned so that no appreciable tensioning of said spring occurs when said limb is straightened, but substantial tensioning thereof occurs when said limb is bent about said joint.

4. The improvement of any preceding claim wherein said artificial limb is an artificial leg and said joint is a knee joint.

5. In an artificial limb including first and second limb members connected for relative pivotal movement about a joint member, a rotator assembly for achieving rotation of said first limb member about an axis extending along its length, said rotator assembly being automatically enabled and disabled for rotation by the relative pivotal movement of said limb members, said rotator assembly comprising:

first and second rotator members on said first limb member mounted to be relatively rotatable about said axis;

locking means, movable between a locking position and a released position, for providing a rigid connection between said rotator members when in said locking position, thereby preventing relative rotation thereof, said locking means being disengaged from at least one of said rotator members when in said released position, thereby permitting relative rotation thereof; and coupling means extending across said joint for providing a mechanical connection between said locking means and a fixed point on said second limb portion;

said limb further including means for transmitting to said coupling means relative pivotal movement of said limb members, to impart movement to said locking member between said locking and released positions, whereby the enablement and disablement of said rotator assembly occur automatically with relative pivotal movement of said limb members.

6. An artificial limb in accordance with claim 5 wherein said rotator members are generally disc-shaped and are mounted in opposed relationship for rotaton about said axis, one of said rotator members having an opening therein, said locking member comprising a plunger mounted on the other rotator member for movement towards and away from said opening said one rotator member, said plunger extending into said opening in said locking position and being external of said opening in said released position.

7. An artificial limb in accordance with claim 1 wherein said locking means includes second resilient means providing a force opposing the force of said first resilient means.

8. An artificial limb in accordance with any one of claims 5-7 wherein said coupling means includes a tension spring forming at least a portion of an elongated coupling member extending across said joint member, said coupling member being positioned so that no appreciable tensioning of said spring occurs when said limb is straightened, but substantial tensioning thereof occurs when said limb is bent about said joint.

9. An artificial limb in accordance with claim 8 wherein said artificial limb is an artificial leg and said joint is a knee joint.

10. An artificial limb in accordance with any of claims 5-9 wherein said artificial limb is an artificial leg and said joint is a knee joint.

11. An artificial limb in accordance with claim 1 wherein said artificial limb is an artificial leg and said joint is a knee joint.

12. An artificial limb in accordance with claim 5 wherein said rotator members are generally tubular and are coaxially mounted for rotation about said axis with said first rotator member extending within said second rotator member, one of said rotator members having an opening therein, said locking member comprising a plunger mounted on the other rotator member for movement towards and away from said opening, said plunger extending into said opening in said locking position and being external of said opening in said released position.

13. An artificial limb in accordance with claim 12 wherein said one rotator member includes a circumferential groove and an axially directed slot intersecting said groove, said plunger having a key portion dimensioned to fit within said groove and said slot, said key position being positioned within said slot when said locking means is in said locking position and said key portion being positioned in said groove when said locking means is in said released position.

14. An artificial limb in accordance with claim 13 wherein said one rotator member is said first rotator member and said groove and slot are on a portion thereof extending with said second rotator member, said second rotator member having an opening extending therethrough aligned with said slot and groove, said plunger being mounted on said second rotator member with said key portion extending through said opening.

15. An artificial limb as in claim 14 wherein said first rotator member further comprises a coaxial shaft portion extending externally of said second rotator member and connected to said second limb member for rotation therewith about said axis, said first rotator member further comprising a sleeve portion mounted on said shaft portion for free rotation with respect thereto, said sleeve portion being coupled to a non-rotating portion of said first limb member.

16. An artificial limb as in claim 15 further comprising cooperating means mounted, respectively, on said shaft and sleeve portions for limiting the amount of relative rotation therebetween.

17. An artificial limb in accordance with any one of claims 5–11 wherein said coupling means includes a first resilient member applying a force to said locking means to achieve movement thereof between said locking and released positions, said force being produced by stressing said resilient member as a result of the relative pivotal movement of said limb members.

* * * * *